United States Patent [19]
Panje

[11] Patent Number: 4,808,183
[45] Date of Patent: Feb. 28, 1989

[54] VOICE BUTTON PROSTHESIS AND METHOD FOR INSTALLING SAME

[75] Inventor: William R. Panje, Iowa City, Iowa

[73] Assignee: University of Iowa Research Foundation, Iowa City, Iowa

[21] Appl. No.: 156,177

[22] Filed: Jun. 3, 1980

[51] Int. Cl.$^4$ .......................... A61F 2/20; A61M 16/00
[52] U.S. Cl. ..................................... 623/9; 128/207.16
[58] Field of Search ..................... 3/1.3, 1; 128/350 R, 128/350 V, 207.16, 274, 1 R; 623/9

[56] References Cited

U.S. PATENT DOCUMENTS

| | | | |
|---|---|---|---|
| 3,263,684 | 8/1966 | Bolton | 128/207.16 |
| 3,747,127 | 7/1973 | Taub | 3/1.3 |
| 3,788,327 | 1/1974 | Donowitz et al. | 128/350 R |
| 3,858,571 | 1/1975 | Rudolph | 128/1 R |
| 3,871,380 | 3/1975 | Heros | 128/350 R |
| 4,037,604 | 7/1977 | Newkirk | 128/350 V |
| 4,044,402 | 8/1977 | Edwards | 3/1.3 |

*Primary Examiner*—Ronald L. Frinks
*Attorney, Agent, or Firm*—Zarley, McKee, Thomte, Voorhees & Sease

[57] ABSTRACT

The voice button prosthesis of the present invention is used for a patient having his larynx removed and having the upper end of his trachea opening through a stoma to the atmosphere. A small opening or fistula is surgically made in the rear of the trachea and in the forward wall of the esophagus so as to provide communication between the interior of the trachea and the interior of the esophagus. The prosthesis comprises an elongated tube adapted to be inserted into the fistual. The tube has a pair of spaced apart flanges adapted to engage the opposite ends of the fistula so as to hold the tube in place. A one way valve is provided in the rearward end of the tube for permitting air to pass from the trachea into the esophagus, and for preventing fluid from passing from the esophagus into the trachea.

12 Claims, 1 Drawing Sheet

U.S. Patent  Feb. 28, 1989  4,808,183
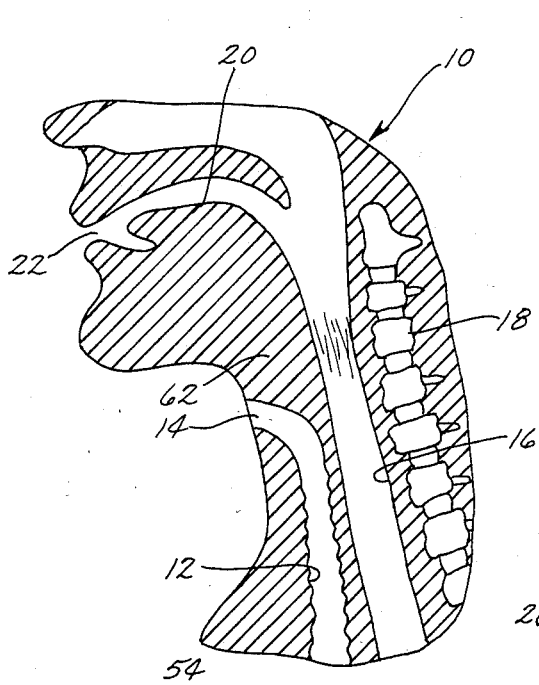
Fig. 1
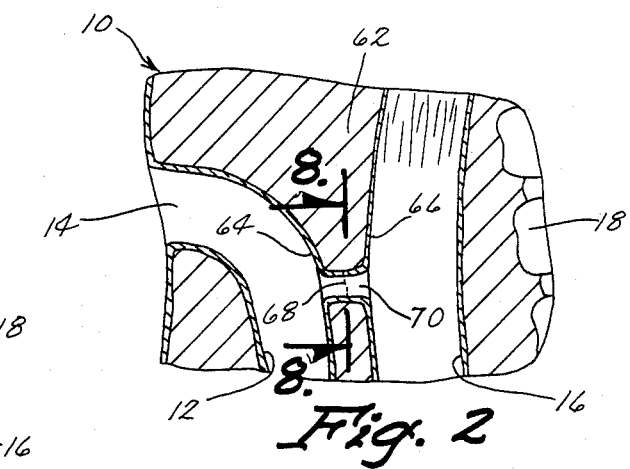
Fig. 2
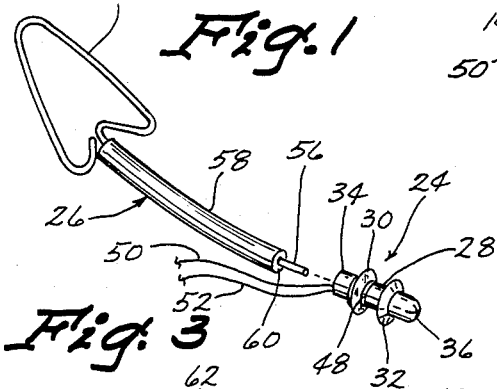
Fig. 3
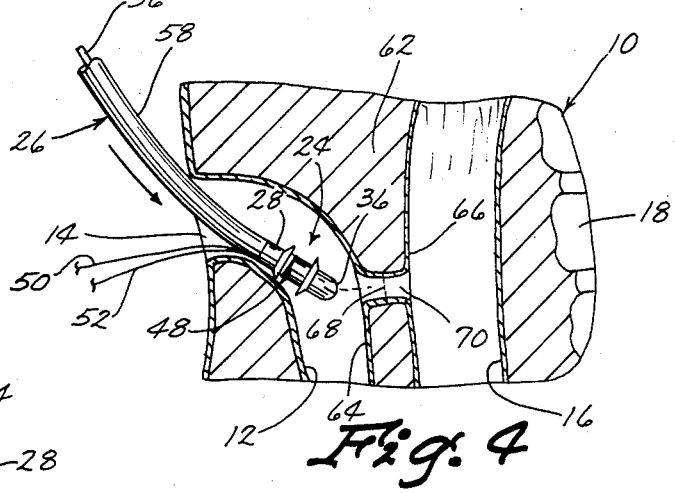
Fig. 4
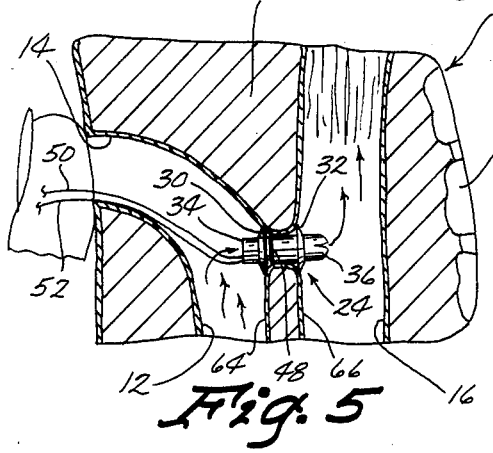
Fig. 5
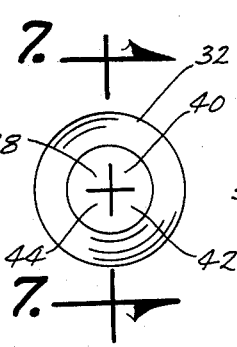
Fig. 6
Fig. 7
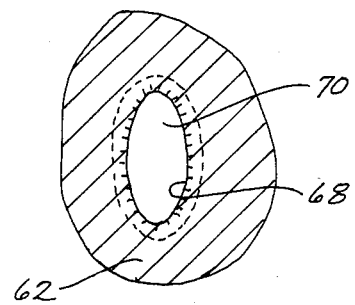
Fig. 8

VOICE BUTTON PROSTHESIS AND METHOD FOR INSTALLING SAME

BACKGROUND OF THE INVENTION

This invention relates to a voice button prosthesis for a patient having his larynx removed.

Many people have their larynx surgically removed as the result of cancer or trauma. Numerous sophisticated operations and devices have been devised to restore the voice in the laryngectomee patient, but these operations are often expensive, require major surgery, and often have a high rate of failure.

It has been found that a voice box or larynx is not essential for speech. The ability of the laryngectomee patient to speak has been restored by surgically providing an opening or fistula between the trachea (windpipe) and the esophagus. The patient can manually close the open upper end or stoma of the trachea, and force air from his lungs through the fistula into the esophagus and upwardly through his mouth. With training, the patient can learn to form words by this process.

However, several disadvantages have been encountered with respect to the above method of restoring speech. The making of an opening between the trachea and the esophagus requires extensive surgery to insure that the opening will stay open and will not close after surgery. Therefore, a general anesthetic is usually used, and the operation is quite expensive.

After the fistula has been made, the patient must have extensive training in order to learn to speak with the above method. The speech requires a hiccuping type action, and at best the speech is of poor quality.

Another disadvantage of the above method is that fluid from the esophagus may enter the trachea through the fistula which has been formed therebetween. Thus, when the patient coughs, or eats, or drinks, there is a problem with fluid or food entering the trachea and causing choking.

There is a high rate of failure (inability of the patient to swallow without aspiration) with the above operation. In such a case, the above method requires additional surgery in order to close the opening. Therefore, the above method is an expensive and cumbersome procedure, and provides unsatisfactory results.

Certain devices have been provided for inserting into the fistula so as to minimize the tendency of the fistula to close. However, these devices are difficult to insert, and the patient is never confident that the device has been inserted to the proper position. Furthermore, some of these devices do not provide satisfactory means for preventing the entry of fluid from the esophagus into the trachea. Many of these devices become dislodged during coughing or movement of the patient. To solve this problem, glue has been applied to the patient's neck in order to secure the prosthesis in place but some patients have had allergic reactions to the glue.

Therefore, a primary object of the present invention is the provision of an improved voice button prosthesis.

A further object of the present invention is the provision of a device which minimizes fluid entry into the trachea with resultant coughing or choking.

A further object of the present invention is the provision of a device which can be installed with minor surgery in a doctor's office, requiring only a local anesthetic.

A further object of the present invention is the provision of a device which minimizes the tendency of the fistula to close.

A further object of the present invention is the provision of a device which enables the patient to speak with little or no training.

A further object of the present invention is the provision of a device which improves the quality of the voice with which the patient can speak.

A further object of the present invention is the provision of a device which is simple to remove and can be removed and cleaned by the patient at will.

A further object of the present invention is the provision of a device which is made of non-irritating material.

A further object of the present invention is the provision of a device which stays in place even during movement, coughing or swallowing of the patient.

A further object of the present invention is the provision of a device which can be inserted by the patient himself so that the patient is confident of its proper positioning.

A further object of the present invention is the provision of a device that needs no material to affix the prosthesis to the person, thereby eliminating the possibility of an allergic or irritative reaction as well as the added inconvenience to the patient.

A further object of the present invention is the provision of a device which is inexpensive and requires less expensive surgical preparation.

A further object of the present invention is the provision of a device which is economical to manufacture, durable in use, and efficient in operation.

BRIEF DESCRIPTION OF THE DRAWINGS

FIG. 1 is a partial sectional view of a patient who has had a laryngectomee.

FIG. 2 is a partial sectional view of FIG. 1 showing a fistula which has been surgically provided between the trachea and the esophagus.

FIG. 3 is a perspective view of the device of the present invention and the tool for inserting same.

FIG. 4 is a view similar to FIG. 2, showing the method of inserting the device into the fistula.

FIG. 5 is a view similar to FIG. 4 showing the device in place.

FIG. 6 is an end view of the device.

FIG. 7 is an end view taken along line 7—7 of FIG. 6.

FIG. 8 is a sectional view taken along line 8—8 of FIG. 2.

DETAILED DESCRIPTION OF THE INVENTION

Referring to FIG. 1, the numeral 10 generally designates a patient having a laryngectomee. The patient's trachea 12 has an open upper end or stoma 14 which opens to the front of the patient's neck. The patient's larynx and epiglottis have been removed and the trachea 12 is completely out of communication with the patient's esophagus 16. The numeral 18 designates the patient's spinal column, the numeral 20 designates the patient's tongue, and the numeral 22 designates the patient's mouth.

The device of the present invention is shown in FIGS. 3 and 7 and is designated generally by the numeral 24. A tool 26 is used to insert the device. Device 24 comprises an elongated tube 28 having an annular tracheal flange 30 and an annular esophageal flange 32 extending radially outwardly from the outer surface thereof. The annular flanges 30 and 32 are formed from flexible material capable of deforming upon being inserted through an opening approximately the same size as elongated tube 28. Tube 28 has a forward end 34 and a rearward end 36. Rearward end 36 has a nose-shape formed by four lips 38, 40, 42, 44 (FIG. 6). These lips form a one way valve which is capable of permitting air to pass through a central bore 46 from forward end 34 towards rearward end 36. Lips 38, 40, 42, 44 are adapted to spread in response to air pressure from within bore 46, but are also adapted to prevent fluid from entering into bore 36 from the outside of rearward end 36.

A thread 48 is looped around tube 28 between flanges 30, 32, and includes a pair of free ends 50, 52 which may be of any desired length for grasping by the patient to remove the device 24 for cleaning.

Tool 26 includes a wire handle 54 and a wire stem 56. Fitted over wire stem 56 is a rubber sleeve 58 having a rearwardly presented shoulder 60 at its end. Shoulder 60 is spaced inwardly from the distal end of wire stem 56. Thus, tube 28 can be fitted on the exposed distal end of wire stem 56 for insertion by the patient. The tool 54 can be released from device 24 merely by withdrawing wire stem 56 from the interior of tube 28.

The surgical preparation of the patient for the insertion of device 24 is shown in FIGS. 2, 4, 5 and 8. The surgeon makes a linear incision in the rearward wall of trachea 14, the incision being approximately 7 mm. long. The incision is made sufficiently deep to provide communication from the interior of trachea 14 to the interior of esophagus 16. Trachea 14 and esophagus 16 are separated by a layer of tissue 62 which is primarily muscle tissue. Trachea 14 is lined with a skin layer referred to as mucosa, which is designated by the numeral 64. Similarly, the esophagus 16 is lined with a mucosa 66. The physician cauterizes the exposed muscle tissue 62 with electrical current or other conventional surgical procedures. After cauterization, the surgeon attaches the mucosa 64 to the mucosa 66 by means of stitching generally designated by the numeral 68, so as to provide a mucosa lining for the entire interior of the opening which has been surgically formed and which is referred to as a tracheo-esophageal fistula 70.

The surgical procedure for forming fistula 70 is simple and can be completed in a doctor's office with local anesthetic. The stitching 68 provides mucosal lining to the interior of fistula 70 so that no "raw tissue" is exposed.

After fistula 70 has been formed, the patient is ready for insertion of prosthesis 24. Device 24 is mounted on the free end of wire stem 56 of tool 26. The patient then grasps handle 54 and inserts device 24 into the trachea 12, through stoma 14, as is shown in FIG. 4. Rearward end 36 of device 24 is inserted into fistula 70 and by means of tool 26 the patient forces device 24 into fistula 70 until it reaches the position shown in FIG. 5. In this position, rearward end 36 and esophageal flange 32 are both completely within esophagus 16. The esophageal flange 32 is sufficiently flexible so as to be deformed for insertion through fistula 70 and for resuming its original shape once inside the esophagus 16 so as to form a sealing engagement with the wall of the esophagus 16 around the fistula 70. Flange 32 fits against the mucosa surrounding fistula 70 so as to provide a seal thereagainst. Flange 30 is completely within trachea 12 and fits in sealing engagement against the mucosa around the esophageal end of fistula 70. Threads 50, 52 trail outwardly through stoma 14 where they may be grasped by the patient to remove device 24 when desired.

In practice it has been found that the patient can readily tell when device 24 is in the proper position shown in FIG. 5. At this time, tool 54 is withdrawn, and the device is completely in place.

When the patient desires to speak, he places his finger or thumb over stoma 14 and forces air upwardly through his trachea 12 in conventional exhaling fashion. The air enters bore 46 of device 24 and forces partial separation of lips 42, 44, 46 as is shown in FIG. 5 so that the air can continue to pass through device 24 into esophagus 16. The air continues to be forced upwardly through the mouth of the patient. It has been found that the patient can form words and speak with little or no training by forcing air upwardly through his esophagus in this fashion. Furthermore, the quality of the speech very closely approximates the quality of speech with the normal larynx. The primary discernable difference is that the patient's voice sounds somewhat hoarse, similar to the way a normal voice would sound during a cold or during laryngitis. Patients have been found to be able to speak in this manner almost immediately after first inserting device 24. This is to be contrasted with other prior devices and methods whereby extensive training was required in order to teach the person to speak.

The lips 38, 40, 42, 44 provide a one way valve means which permits air to pass from the trachea into the esophagus, but which prevents food, water, or other materials to pass from the esophagus into the trachea. In prior devices, a common problem was coughing or choking which occurred when the patient ate or drank. Eating and drinking often caused foreign materials to pass into the patient's trachea, thereby causing coughing or choking.

The device can be inserted easily by th patient, and can be removed merely by grasping thread 50-52 and removing the device from the fistula 70.

Flanges 30, 32 hold the device in place, and the patient soon acquires a confidence that the device will stay in place and will not become dislodged during moving, coughing, swallowing, or drinking.

Other significant advantages of this prosthesis are that it is self-contained within the trachea and is simple to remove or insert. It also requires a minimum of maintenance, and the patient can easily remove the device to clean it or replace it. The device is preferably made of silicone which is a non-irritating material. The device does not dislodge from the opening with swallowing, coughing, or normal head and body movements, and the patient quickly becomes confident of prosthetic position once insertion into the tracheal incision is complete. The device is inexpensive to insert, and is inexpensive to replace. Minimal speech training is needed in order for the patient to speak clearly, and the quality of the speech is superior to that attained with prior devices. The problems previously encountered with former fistulas tending to close after being formed is not present in the present procedure because the device remains inserted within the fistula, thereby preventing closure. Thus, it can be seen that the device accomplishes at least all of its stated objectives.

What is claimed is:

1. A voice button prosthesis for a patient having his larynx removed, said patient having the upper end of his trachea opening through a stoma to the atmosphere through the forward portion of his neck, the patient's esophagus being located behind said trachea, the walls of said trachea and esophagus being separated by a layer of tissue, a tracheo-esophageal fistula being surgically provided through the rear wall of said trachea to provide communication therebetween, said prosthesis comprising:

an elongated tube having an axial forward end and an axial rearward end, said tube being sized to fit within and extend through said fistula with said rearward end in communication with the interior of said esophagus;

a one way valve means being formed at said rearward end of said tube for permitting air to pass through said tube from said trachea to said esophagus while at the same time preventing passage of fluid from said esophagus into said rearward end of said tube;

an annular esophageal flange extending around the outer radial surface of said tube adjacent said valve means and extending radially outwardly therefrom to an outer circumferential edge greater in size than the size of said fistula;

an annular tracheal flange extending radially outwardly from said outer surface of said tube and being spaced axially forwardly from said esophageal flange;

said esophageal flange being sufficiently flexible to be deformed for insertion through said fistula and for resuming its original shape once inside said esophagus so as to form a sealing engagement with the wall of said esophagus around said fistula;

said axial spacing between said tracheal and esophageal flanges being such that said tracheal flange will sealingly engage the interior wall of said trachea around said fistula when said esophageal flange is within said esophagus.

2. A voice button prosthesis according to claim 1 wherein said valve means comprises a flexible nose closing off said rearward end of said tube, said nose having at least one slit therein forming at least two mating flaps which are normally closed against one another and which are yieldably movable apart from one another in response to air pressure from said trachea toward said esophagus.

3. A voice button prosthesis according to claim 2 wherein at least two intersecting slits are formed in said nose so as to form at least four flaps.

4. A voice button prosthesis according to claim 1 wherein a thread is operably secured to said tube and is sufficiently long to extend outwardly through said stoma for grasping by the patient.

5. A method for installing a voice button prosthesis for a patient having his larynx removed and having the upper end of his trachea opening through a stoma to the atmosphere through the forward portion of his neck, said prosthesis comprising an elongated tube having a forward end and a rearward end, a tracheal flange and an esophageal flange extending radially outwardly from said tube and being axially spaced from one another, and one way valve means at said rearward end of said tube for permitting air to exit rearwardly from said tube while at the same time preventing fluid from entering said rearward end of said tube, said method comprising:

surgically making an incision in the patient's trachea and esophagus to form a tracheo-esophageal fistula communicating between the patient's trachea and the patient's esophagus located behind said trachea;

inserting said tube through said fistula to a position wherein said esophageal flange and said valve means are within said esophagus and said tracheal flange is within said trachea.

6. A method according to claim 5 wherein said insertion of said tube is accomplished by placing said tube on one end of an elongated tool, manually inserting said one end of said elongated tool through said stoma into said trachea while grasping the other end of said tool outside said trachea, pushing said tube into said fistula with said tool until said valve means and said esophageal flange are within said esophagus, disengaging said tool from said tube and removing said tool from said trachea.

7. A method according to claim 6 comprising removing said tube from said fistula by grasping threads attached to said tube and extending out through said stoma, said removal being accomplished by manually pulling on said threads to remove said tube from said fistula and outwardly through said stoma.

8. A voice button prosthesis for a patient having his larynx removed, said patient having the upper end of his trachea opening through a stoma to the atmosphere through the forward portion of his neck, the patient's esophagus being located behind said trachea, a tracheo-esophageal fistula of predetermined diameter and axial length being surgically provided through the walls of said trachea and said esophagus to provide communication therebetween; said prosthesis comprising:

an elongated cylindrical tube sized to fit within said fistula and having forward and rearward ends and an axial bore extending therethrough;

one way valve means adjacent said rearward end of said tube for permitting air to pass outwardly from said bore through said rearward end and for preventing fluid from entering into said bore from said rearward end;

a pair of annular flanges spaced axially from one another on the exterior of said tube, each of said flanges extending around the circumference of said tube and extending radially outwardly therefrom to a circumferential diameter which is greater than the diameter of said esophageal fistula, and axial distance between said pair of annular flanges being slightly greater than said axial length of said esophogeal fistula;

at least one of said flanges being sufficiently flexible so as to deform when manually inserted through said fistula and to resume its original configuration once inside said esophagus.

9. A voice button prosthesis according to claim 8 wherein said valve means comprises at least two flexible lip members normally yieldably joined in sealing relationship to close off said bore to fluid passage, said lips being yieldably apart in response to the passage of fluid from said forward end of said bore toward said rearward end of said bore, said lip closing in response to fluid attempting to enter said tube through said rearward end from outside said rearward end of said tube.

10. A voice button prosthesis according to claim 9 wherein said valve means comprises at least four lip members.

11. A voice button prosthesis according to claim 8 wherein said annular flanges are formed from a flexible material capable of deforming upon being inserted through an opening approximately the same size as said tube.

12. A voice button prosthesis according to claim 11 wherein said tube, valve means and flanges are made of silicone.

* * * * *